US011344225B2

United States Patent
Zigel et al.

(10) Patent No.: US 11,344,225 B2
(45) Date of Patent: May 31, 2022

(54) DETERMINING APNEA-HYPOPNIA INDEX AHI FROM SPEECH

(71) Applicants: B. G. Negev Technologies and Applications Ltd., Beer Sheva (IL); Mor Research Applications Ltd., Tel Aviv (IL)

(72) Inventors: Yaniv Zigel, Omer (IL); Ariel Tarasiuk, Meitar (IL); Oren Elisha, Tel Aviv (IL)

(73) Assignees: B. G. NEGEV TECHNOLOGIES AND APPLICATIONS LTD., Beer Sheva (IL); MOR RESEARCH APPLICATIONS LTD., Tel Aviv (IL)

( * ) Notice: Subject to any disclaimer, the term of this patent is extended or adjusted under 35 U.S.C. 154(b) by 0 days.

(21) Appl. No.: 14/762,819

(22) PCT Filed: Jan. 24, 2014

(86) PCT No.: PCT/IB2014/058526
§ 371 (c)(1),
(2) Date: Jul. 23, 2015

(87) PCT Pub. No.: WO2014/115115
PCT Pub. Date: Jul. 31, 2014

(65) Prior Publication Data
US 2015/0351663 A1 Dec. 10, 2015

Related U.S. Application Data

(60) Provisional application No. 61/756,000, filed on Jan. 24, 2013.

(51) Int. Cl.
*G10L 25/66* (2013.01)
*A61B 5/08* (2006.01)
(Continued)

(52) U.S. Cl.
CPC .......... *A61B 5/0826* (2013.01); *A61B 5/4803* (2013.01); *A61B 5/4818* (2013.01);
(Continued)

(58) Field of Classification Search
CPC ... A61B 5/0826; A61B 5/4803; A61B 5/4818; A61B 5/7278; A61B 7/003; G10L 15/00–15/34; G10L 17/00–17/26
See application file for complete search history.

(56) References Cited

U.S. PATENT DOCUMENTS 6,401,063 B1 * 6/2002 Hebert ............... G10L 17/04
704/234
6,993,380 B1 * 1/2006 Modarres ............... A61B 5/048
600/544
(Continued)

FOREIGN PATENT DOCUMENTS

WO 2012025892 3/2012

OTHER PUBLICATIONS

Goldshtein-E et al.; Automatic Detection of Obstructive Sleep Apnea Using Speech Signals; IEEE Transactions on Biomedical Engineering, vol. 58, No. 5, pp. 1373-1382. May 2011 (Year: 211).*
(Continued)

*Primary Examiner* — Abul K Azad
(74) *Attorney, Agent, or Firm* — Nixon & Vanderhye PC (57) ABSTRACT

A method of determining a value for an apnea-hypopnea index (AHI) for a person, the method comprising: recording a voice track of a person; extracting features from the voice track that characterize the voice track; and processing the features to determine an AHI.

15 Claims, 4 Drawing Sheets

(51) Int. Cl.
  *A61B 7/00* (2006.01)
  *A61B 5/00* (2006.01)
(52) U.S. Cl.
  CPC ............ *A61B 5/7278* (2013.01); *A61B 7/003* (2013.01); *G10L 25/66* (2013.01)

(56) References Cited

U.S. PATENT DOCUMENTS

| | | | | |
|---|---|---|---|---|
| 2002/0193697 | A1* | 12/2002 | Cho | A61B 5/0205 600/529 |
| 2008/0147391 | A1* | 6/2008 | Jeong | G10L 15/02 704/232 |
| 2009/0043586 | A1* | 2/2009 | MacAuslan | G10L 25/48 704/270 |
| 2009/0318773 | A1* | 12/2009 | Jung | A61B 5/4064 600/300 |
| 2010/0217133 | A1* | 8/2010 | Nilsen | A61B 5/0205 600/484 |
| 2010/0280827 | A1* | 11/2010 | Mukerjee | G10L 15/142 704/236 |
| 2012/0065974 | A1* | 3/2012 | Hagai | G06F 17/5045 704/246 |
| 2012/0271199 | A1* | 10/2012 | Salisbury | A61B 5/4818 600/586 |
| 2013/0253357 | A1* | 9/2013 | Moussavi | A61B 5/4818 600/529 |

OTHER PUBLICATIONS

Elisha et al.; Detection of Obstructive Sleep Apnea using Speech Signal Analysis; Models and analysis of vocal emissions for biomedical applications, pp. 13-16, 7th international workshop, Aug. 25-27, 2011 (Year: 2011).*
Debasish Basak et al. "Support Vector Regression" Neural Information Processing—Letters and Reviews Oct. 2007, vol. 1 No. 10, pp. 203-224.
Tobias Booklet et al. "Age Determination of Children in Preschool and Primary School Age with GMM-based Supervectors and Support Vector Machines/Regression", Lecture Notes in Computer Science; vol. 5246, 2008; pp. 1-9.
Harris Drucker et al. "Support Vector Regression Machines", MIT Press. 1996.
O. Elisha et al. "Automatic Detection of Obstructive Sleep Apnea Using Speech Signal Analysis", Afeka-AVIOS Speech Processing Conference, 2012.
International Search Report dated Aug. 5, 2014 for corresponding PCT/IB14/58526, Filing date Jan. 24, 2014.

* cited by examiner

DETERMINING APNEA-HYPOPNIA INDEX AHI FROM SPEECH

RELATED APPLICATIONS

The present application is a U.S. National Phase of PCT/IB2014/058526 filed on Jan. 24, 2014, which claims the benefit under 35 U.S.C 119(e) from U.S. Provisional application 61/756,000 filed on Jan. 24, 2013. The contents and disclosures of these prior applications are incorporated herein by reference in their entirety.

TECHNICAL FIELD

Embodiments of the invention relate assessing sleep quality.

BACKGROUND

Sleep disorders appear to be quite widespread, and complaints and worries about real or imagined sleep disorders and levels of discomfort with respect to how much sleep one gets and quality of sleep are common subjects for discussion. It is estimated that between 40% and 60% of the population in modern societies are affected, or possibly believe they are affected to some degree by sleep disorder. Real sleep disorders can be serious and may be considered to be disease conditions on their own and/or can lead to disease conditions that interfere with normal physical, mental, and/or emotional functioning.

By way of example, it is estimated that 60% of the adult population suffer from insomnia, 30-70% suffer from snoring, and between 2% to 7% of the population suffer from obstructive sleep apnea (OSA). OSA is characterized by repetitive collapse or narrowing of the upper airway passages during sleep that impairs ventilation, may lead to total or near total cessation of breathing and disrupts sleep. OSA events are typically associated with episodes of snoring that may be followed by long silent periods during which there is no breathing. The periods of no breathing are typically followed by neurological arousal of the person from sleep that initiates activity to reopen the upper airway passages and reestablish breathing. The activity to reestablish breathing is generally accompanied by relatively intense, loud snorts and/or gasps as the person struggles to regain breathing.

Sleep disorders can result in a spectrum of undesirable effects that includes besides anxiety, daytime drowsiness, and impairment of concentration and motor functions, potentially relatively long term serious health risks. For example, OSA is associated with increased cardiovascular morbidity.

Conventionally, diagnosing a person's sleep disorders, and in particular OSA, involves performing a sleep study, referred to as polysomnography, (PSG). PSG is a relatively complicated and expensive procedure that is carried out in a sleep laboratory during an overnight stay of the person in the laboratory. PSG typically involves attaching a variety of sensors to the person's body to generate "PSG signals" during a sleep period of the person's overnight stay. The PSG signals track performance of a battery of physiological activities and functions that may be used to determine presence of episodes, "OSA events", of complete and/or partial cessation of breathing during the sleep period. The tracked activities and functions may include brain activity, eye motion, skeletal muscle activation, respiratory efforts, and heart function during sleep.

Presence and/or severity of OSA is conventionally measured by an apnea-hypopnea index (AHI), which is simply a count of a number of OSA events that a person experiences per hour of sleep. A person is generally considered to have OSA if he or she has an AHI greater than or equal to 5, that is, evidences 5 or more OSA events per sleep hour. A person having an AHI between 5 and 14 is considered to have mild OSA and moderate OSA if he or she has an AHI between 15 and 29. A person having an AHI of 30 or more is considered to have severe OSA.

In addition to being uncomfortable, expensive, and equipment intensive, PSG studies to determine quality and disturbances of a person's sleep are not readily accessible. It is estimated for example, that the waiting period for PSG has been reported to be a few weeks to more than a year in the United States.

SUMMARY

An aspect of an embodiment of the invention relates to determining a measure of AHI for a person responsive to features extracted from a recording of a vocal track of the person's speech. Optionally, the extracted features are processed to provide a plurality of feature vectors for each of a plurality of phonemes, words, and/or sentences in the voice track. The plurality of feature vectors for each of the phonemes may be processed to determine a set of mean feature vectors of a Gaussian mixture model (GMM) that provides a probability density distribution for the phoneme's feature vectors. Optionally, the phonemes are phonemes characteristic of the vowels /a/, /e/, /i/, /o/, /u/ and phonemes characteristic of nasal consonants /m/ and /n/. In an embodiment of the invention a posteriori mean estimate is determined for the mean of each feature vector responsive to a universal background Gaussian mixture model probability density distribution and the mean feature vector. The posteriori mean estimates for all the phonemes and a feature vector for the vocal track are optionally concatenated to form a super vector. A value for the AHI for the person is determined responsive to the super vector and a support vector regression.

In the discussion, unless otherwise stated, adjectives such as "substantially" and "about" modifying a condition or relationship characteristic of a feature or features of an embodiment of the invention, are understood to mean that the condition or characteristic is defined to within tolerances that are acceptable for operation of the embodiment for an application for which it is intended. Unless otherwise indicated, the word "or" in the description and claims is considered to be the inclusive "or" rather than the exclusive or, and indicates at least one of, or any combination of items it conjoins.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

BRIEF DESCRIPTION OF FIGURES

Non-limiting examples of embodiments of the invention are described below with reference to figures attached hereto that are listed following this paragraph. Identical structures, elements or parts that appear in more than one figure are generally labeled with a same numeral in all the figures in which they appear. A label labeling an icon representing a given feature of an embodiment of the invention in a figure may be used to reference the given feature. Dimensions of components and features shown in the figures are chosen for convenience and clarity of presentation and are not necessarily shown to scale.

DETAILED DESCRIPTION

Figure 1A:
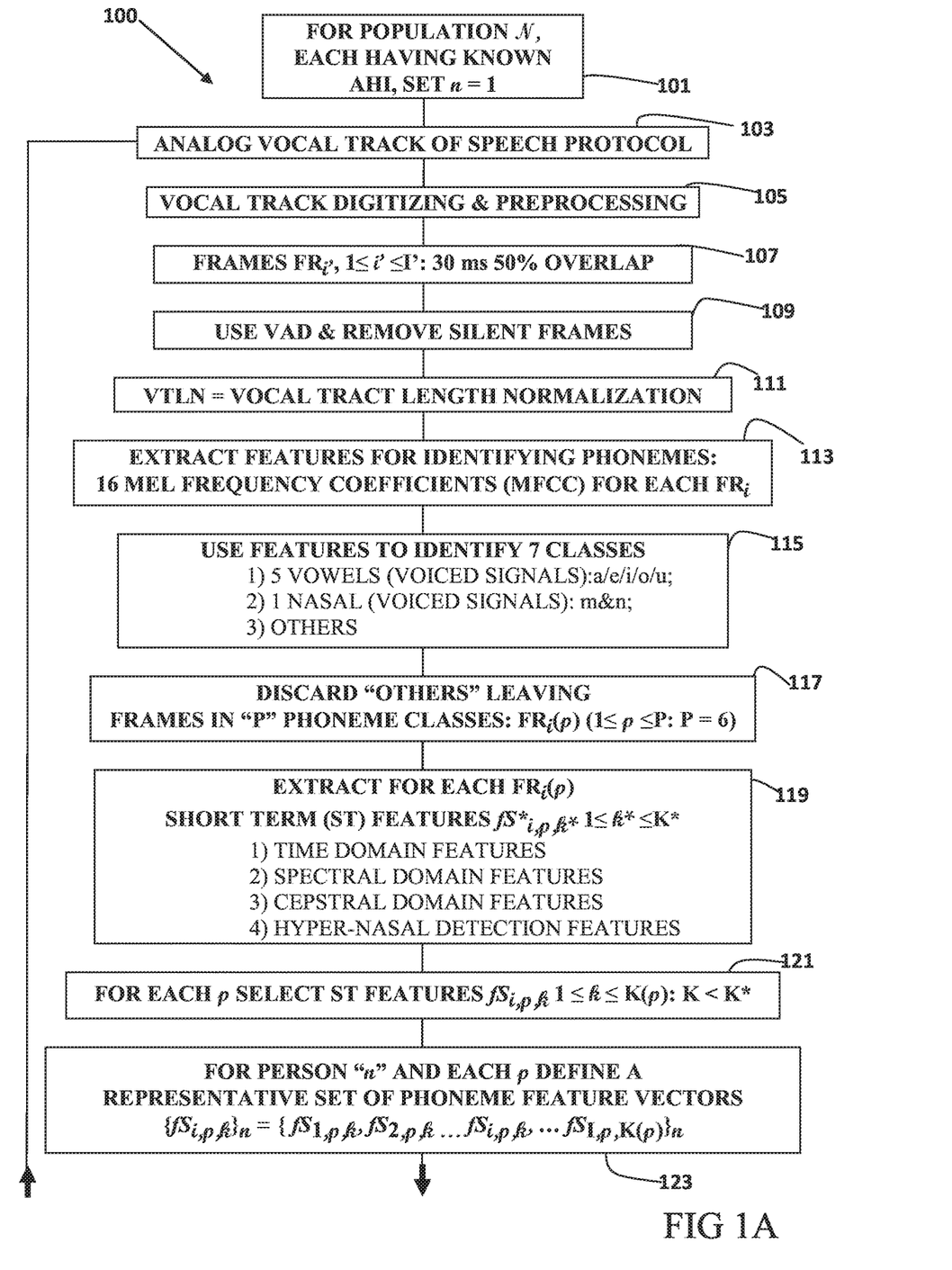
FIGS. 1A-1C show a flow diagram of a method of determining AHI or diagnosing presence of OSA, in accordance with an embodiment of the invention.
Figure 1B:
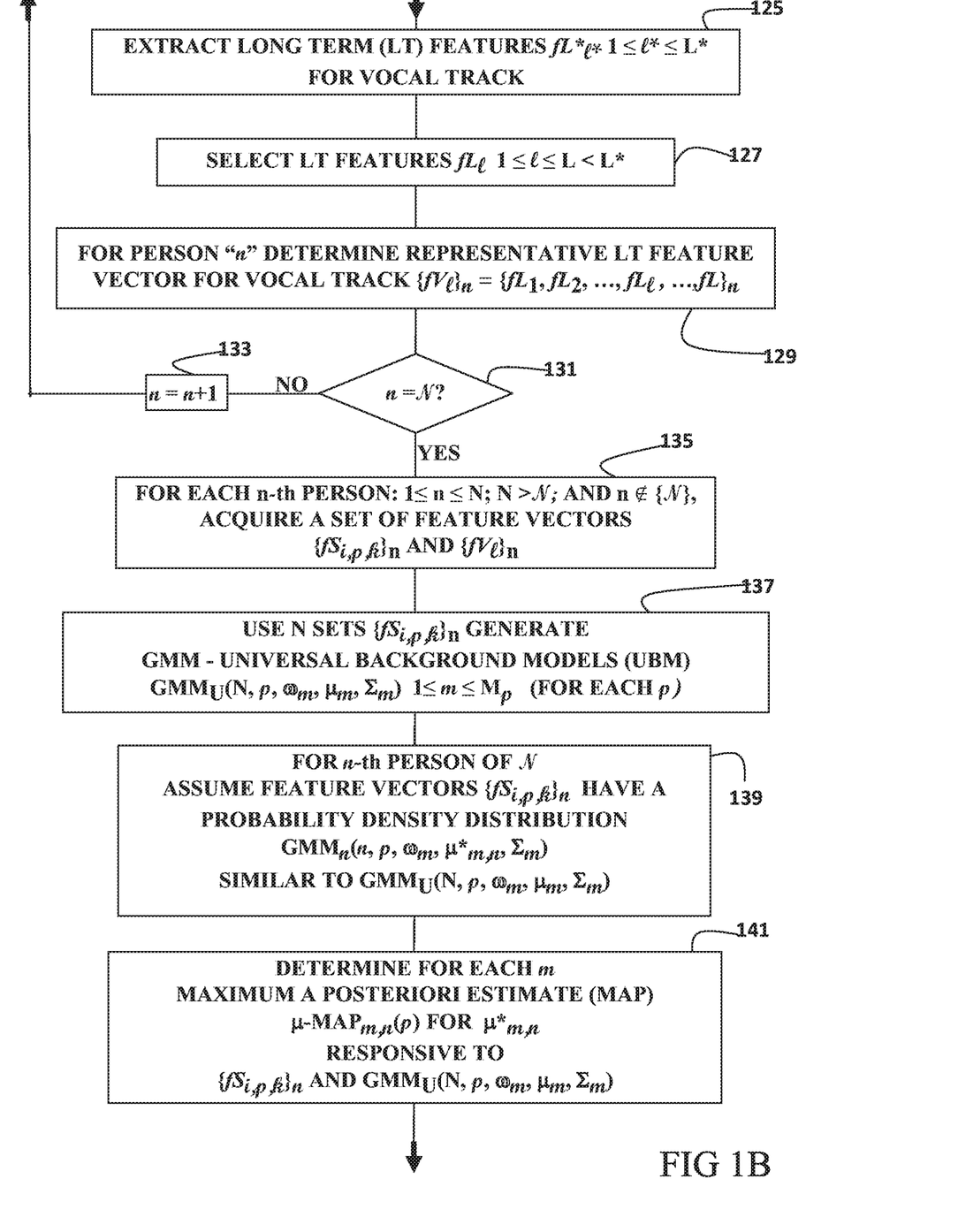
Figure 1C:
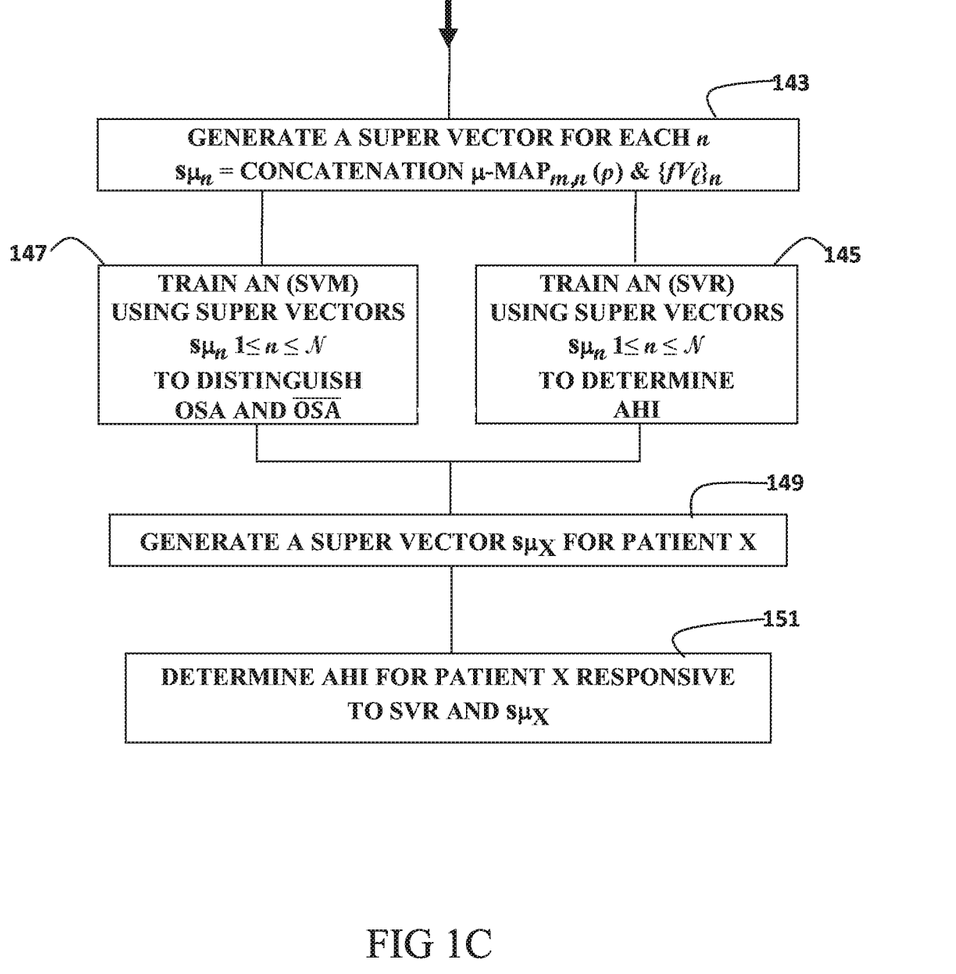

FIG. 1 shows a flow diagram of an algorithm 100 for determining an AHI for a patient "X" responsive to a voice track of the patient's voice, in accordance with an embodiment of the invention.

In a block 101 a value for an index a that indexes persons in a population of $\mathcal{N}$ person is set to 1. In a block 103 an analog voice track of a first person, n=1, of the group of $\mathcal{N}$ persons is recorded voicing a speech protocol comprising utterances that may be used to determine whether a person has OSA, and if so severity of OSA. The voice track may be recorded using at least one or any combination of more than one of any suitable sound recording instruments, such as by way of example, a Handy H4 digital recorder by ZOOM, or a microphone comprised in a smart phone, PC (personal computer), laptop or tablet. The at least one sound recording instrument may comprise a contact microphone that is optionally mounted to the neck of the person and or a stereo recording system. Optionally the at least one recording instrument comprises a recording system that records an amount of acoustic energy that passes through and radiates from a person's mouth and/or nasal passages in producing sounds recorded in the voice track.

In an embodiment of the invention, the speech protocol comprises phonemes whose utterances are affected by features of the human voice tract that distinguish persons suffering from OSA from persons that do not suffer from OSA. The protocol may be configured so that the recorded voice track includes phonemes characteristic of utterances of the vowels /a/, /i/, /u/, /e/, /o/, and nasal consonants, /m/ and /n/, also referred to as "nasals".

In a block 105 the analog voice track is digitized and preprocessed. Preprocessing may include DC removal, down sampling the voice track from a sampling rate at which the analog voice track was recorded, and removal of lip-radiation effects. In an embodiment of the invention an analog voice track may be recorded at a sampling rate of about 44 kHz (kilohertz) and down sampled to optionally about 16 kHz. Lip radiation effects may be reduced by filtering the voice track using a suitable finite impulse response filter (FIR).

In a block 107, the voice track may be divided into frames, represented by $FR_{i'}$, $1 \leq i' \leq I'$, optionally having duration between about 20 ms and 60 ms (milliseconds) and overlap equal to about 50%. Optionally, the frames are windowed using any of various window functions known in the art, such as by way of example, the common Hamming window function. In a block 109 silent frames are identified using a suitable voice activity detector (VAD) and removed, leaving "I-" frames remaining.

In a block 111 the frequency spectrums of portions of the vocal track respectively comprised in frames $FR_i$ are corrected for vocal tract length of the person. Formants, which are spectral peaks in the frequency spectrum of a person's speech, may be used to distinguish vowels in the speech and are generally shifted to lower frequencies with increasing vocal tract length. In an embodiment of the invention, the vocal tract length correction normalizes the formant frequencies to a "standard" vocal tract length so that the normalized formants are substantially independent of vocal tract length and are more readily recognized as markers of the person's vocalization of vowels. Hereinafter, a portion of the vocal track comprised in a frame may be referred to as a "frame voice signal", or a voice signal of a frame.

Optionally, the vocal tract length of a person is estimated from images of the person's face and neck. The images may be acquired using any of various suitable cameras, and may for example, comprise a camera included in a smartphone, laptop, or tablet, or a 3D (three dimensional) camera that may be operated to acquire a three dimensional 3D image of a person.

In a block 113 frames $FR_i$ are processed to extract features from the frames that may be used for associating the frames with particular phonemes. In an embodiment of the invention, the features comprise, optionally 16, mel-frequency cepstral coefficients (MFCCs). The mel frequency scale is a perceptual scale of frequencies, measured in "mels", that maps frequency conventionally measured in Hz to a perceptual scale for which pairs of pitches having a same difference in mels are perceived by a human as having a same difference in frequency, or pitch. A frequency "$f_{Hz}$" in Hz has a frequency "$f_{mel}$" in mels defined by a formula: $f_{mel}=2595 \log 10(1+f_{Hz}/700)$. The MFCCs, for a given frame $FR_i$ are Fourier coefficients of a discrete mel-frequency power spectrum of a portion, the frame voice signal, of the vocal track comprised in $FR_i$.

In a block 115 the extracted features are used to associate each frame $FR_i$ with optionally one of seven classes of phonemes. The seven classes may include five classes of phonemes that are exhibited respectively in utterances of the five vowels, /a/, /i/, /u/, /e/, /o/, a class /m/&/n/ of nasal phonemes comprising the phonemes /m/ and /n/, and a class of "others", with which a frame is associated if it is not associated with any of the other classes. Optionally, the association is performed in accordance with a suitable classifier such as a Gaussian mixture model (GMM) or a k-nearest neighbor (KNN) classifier. In a block 117 frames associated with "others" are discarded leaving a set of "I" frames $FR_i$, $1 \leq i \leq I$, classified as associated with one of six phoneme classes /a/, /i/, /u/, /e/, /o/, and /m/&/n/ respectively indicated and referred to by an index p, $1 \leq p \leq 6$.

In a block 119 short term (ST) features, $fS^*_{i,p,k}*$, $1 \leq k^* \leq K^*$, that may be used to characterize the frames and determine presence and severity of OSA are extracted for each frame $FR_i$. In an embodiment of the invention features $fS^*_{i,p,k}*$ may comprise at least one feature from one or any combination of more than one of, time domain features, spectral domain features, cepstral domain features, and/or hyper-nasal features. Optionally K* is greater than or equal to about 50. Optionally K* is greater than or equal to about 75. K* may be greater than or equal to about 100.

Time domain features may by way of example comprise energy, pitch, jitter, and shimmer exhibited by a voice signal in a frame. Energy may be an average of energy of the voice signal in a frame over duration of the frame. Pitch associated with a frame may be a fundamental sound frequency exhibited by the frame voice signal or voice signals in a sequence of consecutive frames comprising the frame that are associated with a same phoneme. Jitter may be a measure of variance of a fundamental period exhibited by the voice signal in a frame or voice signals in a sequence of consecutive frames comprising the frame that are associated with a same phoneme. Shimmer may be a measure of variance in peak to peak amplitude of sound exhibited by the voice signal in a frame or voice signals in a sequence of consecutive frames comprising the frame that are associated with a same phoneme. Spectral features may, by way of example, comprise linear predictive coding coefficients (LPC) and derivatives thereof, formant location and bandwidth, auto regressive moving average (ARMA) coefficients that are characteristic of a frame voice signal. Cepstrum domain features may comprise MFCCs and derivatives of MFCCs.

Hyper-nasal features may comprise a Teager energy difference, a LPC difference, and a standard deviation of a power spectral density (PSD) of a voice signal in a frame. The Teager energy difference for a frame may be a difference between values for the Teager energy operator (TEO) applied to first and second "Teager signals" generated from the frame voice signal. The first Teager signal may be the frame voice signal filtered by a finite impulse response band pass filter centered at a first formant of the frame voice signal. The second Teager signal may be the frame voice signal filtered by a low pass filter that removes frequencies higher than the first formant for the frame voice signal. The LPC difference feature for a frame may be a square of the Euclidean distance between linear predictive coefficients determined for low and high order LPC models of the frame voice signal. The standard deviation of PSD for a frame may be determined for frequencies of the frame voice signal between about 300 Hz and about 2000 Hz.

The following table provides a list of $K^*=103$ short term features that may be extracted from frames in accordance with an embodiment of the invention.

| # | Feature name | No. of features | Feature symbol |
|---|---|---|---|
| 1 | Fundamental Frequency | 1 | $F_0$ |
| 2 | Jitter | 1 | Jitt |
| 3 | Shimmer | 1 | Shimm |
| 4 | Vocal tract length | 1 | VTL |
| 5 | Harmonic to noise ratio | 1 | HNR |
| 6 | Formants | 3 | $F_1$-$F_3$ |
| 7 | Formants derivative ($F_2$-$F_1$, $F_3$-$F_2$) | 2 | $DF_{12}$, $DF_{23}$ |
| 8 | Formant Band width | 3 | $BW_1$-$BW_3$ |
| 9 | Linear prediction coding (LPC) | 18 | $a_1$-$a_{18}$ |
| 10 | ARMA model | 18 | $ar_1$-$ar_{18}$ |
| 11 | Mel frequency cepstral coef. (MFCC) | 16 | $c_1$-$c_{16}$ |
| 12 | ΔMFCC | 16 | $\Delta c_1$-$\Delta c_{16}$ |
| 13 | ΔΔMFCC | 16 | $\Delta\Delta c_1$-$\Delta\Delta c_{16}$ |
| 14 | Energy | 1 | E |
| 15 | ΔEnery | 1 | ΔE |
| 16 | ΔΔEnergy | 1 | ΔΔE |
| 17 | Teager energy operator | 1 | TEO |
| 18 | High and low order LPC difference | 1 | LPCdiff |
| 19 | Standard deviation of PSD | 1 | PSD-STD |

In a block 121, optionally a same subset of K features $f^S{i,p,k}$ $1\leq k \leq K(p)<K^*$ is selected from the $K^*$ features $fS^*_{i,p,k}$ $1\leq k^* \leq K^*$ for each frame identified with a same phoneme for use in determining presence of OSA and/or AHI. In an embodiment of the invention, a selection algorithm for selecting features $f^S{i,p,k}$ may be dependent on phoneme index $p$, and a number and/or identity of selected features $f^S{i,p,k}$ for a frame may therefore be dependent on the frame's phoneme index $p$, as indicated by writing K as $K(p)$ above and in block 121. As a result, features selected for frames associated with a first of the phonemes may be different from a set of features selected for frames associated with a second of the phonemes. For example, the features selected for frames identified with phoneme /a/ referred to by index $p=1$ may be different in number and/or identity from features selected for frames identified with phoneme /u/ referred to by index $p=5$. Optionally a selection algorithm used to select features $f^S{i,p,k}$ selects $K(p)$ features from among the $K^*$ features that perform best as measured by a suitable performance criterion in reducing error in determining AHI and/or presence of OSA. Optionally, a sequential forward floating selection (SFFS) and/or a leave one out (LOO) algorithm is used to choose the $K(p)$ features.

Following selection of feature vectors $f^S{i,p,k}$, optionally in a block 123, the n-th (at this point in the description of algorithm 100, n=1) person is associated with a representative set of short term feature vectors: $\{f^S{i,p,k}\}_n = \{f^S{i,p,k}, f^S{2,p,k} \ldots f^S{i,p,k}, \ldots f^S{I,p}, K(p)\}_n$ ($p=1\rightarrow 6$).

It is noted that whereas selection is shown in block 121 following block 119, order of blocks in flow diagram 100 does not determine an order in which actions noted in the blocks are undertaken. In particular, selection noted in block 121 may be performed after acquiring and processing a number of voice tracks from different persons having known states of OSA sufficient to provide models and statistics useable to grade performance of different features $fS^*_{i,p,k}*$ in determining OSA and AHI. For example, selection may be performed only after acquiring and processing voice tracks for $\mathcal{N}$ persons, realizing a "YES" in decision block 131, discussed below, and using feature vectors $fS^*_{i,p,k}*$ to generate GMM distributions for testing performance of different combinations of feature vectors $fS^*_{i,p,k}*$ in determining presence of OSA and/or AHI.

In blocks 125-129 (FIG. 1B), optionally following selection of short term vector set $\{f^S{i,p,k}\}_n$, algorithm 100 extracts, selects, and associates long term (LT) feature vectors with the n-th person. In block 125, LT feature vectors $fL^*_{l^*}$ $1\leq l^* \leq L^*$ are extracted for the vocal track of the person. Long term feature vectors comprise feature vectors that are determined responsive to voice signals in a plurality of frames associated with different phonemes and/or all the frames associated with phonemes in the vocal track recorded for the person. The long term features may for example comprise values for statistical parameters of short term features of the voice track such as a mean vocal track length over a plurality of different frames and different phonemes, a mean harmonic to noise ratio, a vowel space area for each of the vowels /a/, /i/, /u/, /e/, /o/, a difference between the first and second formants, F1 and F2, for each vowel, and a difference between the second and third formants, F2 and F3, for each vowel. Long term features may also include physical characteristics of the person such as body mass index (BMI), gender, and age.

The following table provides a list of long term features that may be determined for the vocal track of the person in accordance with an embodiment of the invention.

| # | Feature name | No. of features | Feature symbol |
|---|---|---|---|
| 1 | Mean VTL | 1 | MVTL |
| 2 | Mean HNR | 1 | MHNR |
| 3 | Vowel Space Area, $F_1$-$F_2$ and $F_2$-$F_3$ Space | 2 (1 × 2) | $A_{12}$, $A_{23}$ |

-continued

| # | Feature name | No. of features | Feature symbol |
|---|---|---|---|
| 4 | Center of mass, $F_1$-$F_2$ and $F_2$-$F_3$ Space | 4 (2 × 2) | $CM_{12}$, $CM_{23}$ |
| 5 | Distance from Center of Mass of each vowel, $F_1$-$F_2$ and $F_2$-$F_3$ Space | 10 (5 × 2) | $DCM_{12}$, $DCM_{23}$ |
| 6 | Difference between $F_1$ and $F_2$ for each vowel | 5 | $DF_{12}$ |
| 7 | Difference between $F_2$ and $F_3$ for each vowel | 5 | $DF_{23}$ |

In a block 127, optionally a subset of L long term features $fL_l$ $1 \leq l \leq L < L^*$ is selected from the $L^*$ features $fL^*_{l^*}$ $1 \leq l^* \leq L^*$ associated with the person's vocal track for use in determining presence of OSA and/or AHI. Selected long term features $fL_l$ may be selected similarly to the way described above in which short term features are selected. Optionally in a block 129, the n-th (again noted, at this stage n=1) person may be associated with a representative long term feature vector: $\{fV_l\}_n = \{fL_1, fL_2, \ldots, fL_l, \ldots, fL\}_n$.

In a decision block 131, n is checked to determine if it is equal to $\mathcal{N}$. If it is not, algorithm 100 optionally proceeds to a block 133, increases n by 1 and returns to block 103 to acquire feature vectors $\{f^{S_i,p,k}\}$ and $\{fV_l\}$ for another person. If on the other hand n is equal to $\mathcal{N}$ and the algorithm has acquired feature vectors $\{f^{S_i,p,k}\}$ and $\{fV_l\}$ for each of the population of $\mathcal{N}$ persons, the algorithm proceeds to a block 135.

In block 135, a set of feature vectors $\{f^{S_i,p,k}\}_n$ and $\{fV_l\}_n$ ($1 \leq n \leq N$) is acquired for each "n-th" person of a relatively large "background" population of "N" persons for which presence or absence of OSA is not generally, but may, be known. In a block 137, the N sets of feature vectors are used to generate a Gaussian universal background mixture model $GMM_U(N, p, \omega_m, \mu_m, \Sigma_m)$ $1 \leq m \leq M_p$, for each phoneme $p$, where $M_p$ is a number of Gaussians in the model for the $p$-th phoneme, $\mu_m$ is a mean feature vector of the feature vectors for the m-th ($1 \leq m \leq M_p$) Gaussian, $\Sigma_m$ is an associated covariance matrix, and $\omega_m$ is a weighting factor for the m-th Gaussian.

In a block 139, it is assumed that the phoneme feature vectors $\{f^{S_i,p,k}\}_n$ for the $p$-th phoneme of the n-th person of the population of $\mathcal{N}$ persons having known states of OSA has a probability density function that may be described by a Gaussian mixture model $GMM_n(n. p, \omega_m, \mu^*_{m,n}, \Sigma_m)$ similar to $GMM_U(N, p, \omega_m, \mu_m, \Sigma_m)$. In a block 141, a maximum posteriori (MAP) estimate, $\mu$-$MAP_{m,n}(p)$, is determined for each $\mu^*_{m,n}$ responsive to $GMM_U(N, p, \omega_m, \mu_m, \Sigma_m)$ and $\{f^{S_i,p,k}\}_n$. In a block 143 (FIG. 1C) the n-th person is associated with a super vector $s\mu_n$, which is a concatenation of the long term feature vector $\{fV_l\}_n$ and the MAP vectors $\mu$-$MAP_{m,n}(p)$ for all the phonemes—that is for $p=1, 2, \ldots, P$, which, as described above is optionally equal to 6.

In a block 145 the $\mathcal{N}$ super vectors $s\mu_n$ and there known OSA statuses are optionally used to train a support vector regression (SVR) machine to determine an AHI for a given patient responsive to a super vector determined in accordance with an embodiment of the invention, similarly to the manner in which a super vector $s\mu_n$ is determined. In a block 147, the $\mathcal{N}$ super vectors $s\mu_n$ and their known OSA statuses may also be used to train a support vector machine (SVM) to distinguish whether or not a given patient has OSA or not, responsive to a super vector determined for the patient in accordance with an embodiment of the invention.

In a block 149 a super vector $s\mu_X$ is determined for patient X in accordance with an embodiment of the invention, similarly to the manner in which a super vector $s\mu_n$ is determined. Optionally, in a block 151 an AHI is determined for patient X responsive to the SVR determined in block 145 operating on super vector $s\mu_X$.

Figure 2:
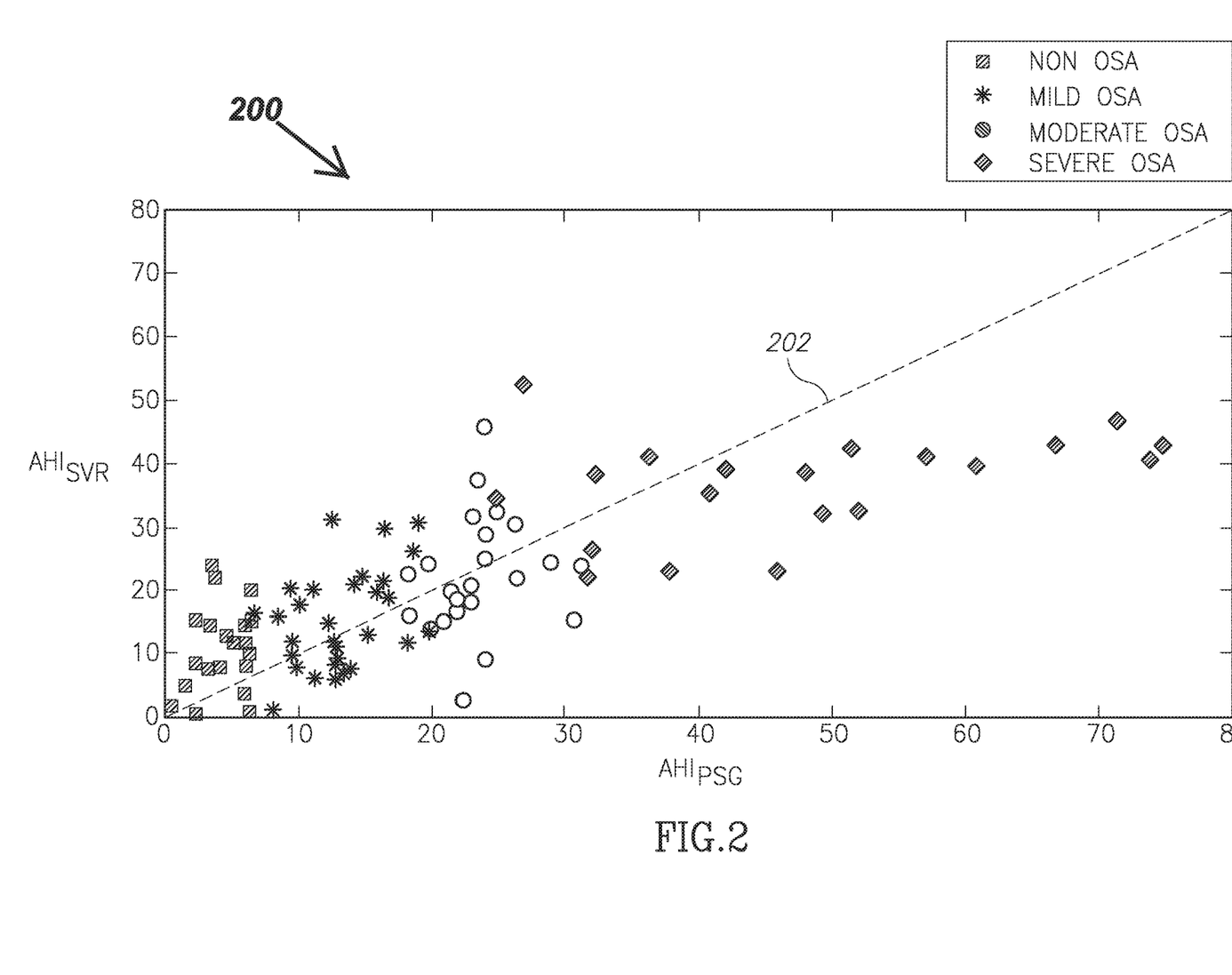
FIG. 2 shows a graph comparing diagnoses of AHI by PSG and a method in accordance with an embodiment of the invention.

FIG. 2 shows a graph 200 that compares values for AHI determined for a population of men by PSG and an SVR machine generated in accordance with an algorithm similar to algorithm 100 for a relatively small population of about 100 men, in accordance with an embodiment of the invention. Values of AHI determined by PSG are shown along an abscissa of the graph labeled $AHI_{PSG}$ and values determined by the SVR are shown along an ordinate of the graph labeled $AHI_{SVR}$. The graph shows values of AHI determined by PSG and SVR for four groups of patients. Patients represented by shaded squares, asterisks, empty circles, and shaded diamonds were determined by PSG to exhibit no OSA, mild OSA, moderate OSA, and severe OSA respectively. The graph shows relatively good agreement between PSG and SVR diagnoses. Diagnoses for which PSG and SVR values are substantially identical lie on or near to a dashed line 202.

Whereas in the above description of algorithm 100 a person's voice track was segmented into frames which were classified into a particular set of phonemes—namely the vowel phonemes and nasal phonemes- to generate super vectors, practice of the invention is not limited to processing voice tracks in accordance with algorithm 100 to determine AHI.

For example, in an embodiment of the invention, frames from a person's voice track may not be classified by association with phonemes. Instead, values for a same set of ST features independent of phoneme identification are extracted for each non-silent frame and used to provide a short term feature vector for frame. A phoneme-anonymous feature vector may be generated for the person by concatenating a plurality of the ST feature vectors and optionally concatenating the concatenated ST feature vectors with a long term feature vector of the person. The phoneme-anonymous feature vector for each of a relatively large background population, N, may be used to determine a $GMM_{UBM}$. The $GMM_{UBM}$ and phoneme-agnostic feature vectors for persons in a population $\mathcal{N}$ having known states of OSA may be used to determine "MAP" mean feature vectors for each of the $\mathcal{N}$ persons. Super vectors generated from the MAP vectors may be used to train an SVR machine for determining AHI, or an SVM machine for determining presence or absence of OSA.

In an embodiment of the invention, an estimate of AHI may be produced without use of super vectors. Short term feature vectors extracted from vocal track frames for persons in a population $\mathcal{N}$ having known states of OSA may be used to train a Gaussian mixture regression (GMR) model for determining AHI for each of a plurality of a set of different phonemes. To determine AHI for a patient X, feature vectors are extracted from a voice track recorded for the patient for frames associated with each of the different phonemes. An AHI value is determined for each of the phonemes responsive to the extracted feature vectors for the phoneme. An AHI for patient X is determined as an optionally weighted average of the AHI values.

Furthermore, classifiers other than Gaussian mixture classifiers may be used to determine in accordance with an embodiment of the invention whether features of a voice track indicate a given AHI for a person. A neural network may be taught to determine AHI for a person responsive to an ensemble of feature vectors generated from the person's voice track. Or, linear regression may be used to provide a diagnosis of AHI. Linear regression may be performed for example on super vectors $\{f^{S}i,p,k\}_n$ determined in block 123 of algorithm 100 optionally having a relatively small subset of less than about 5 features for persons in a population $\mathcal{N}$ having known states of OSA.

In an embodiment of the invention, an algorithm for processing a voice track recorded for a person to determine an AHI for the person in accordance with an embodiment of the invention may be performed by any of various computer systems executing a suitable computer executable instruction set.

For example, as noted above, a recording device for acquiring a voice track of a person for processing to determine an AHI for the person may comprises a microphone housed in a smart phone, PC (personal computer), or in a laptop or tablet computer. Optionally, the executable instruction set for processing the voice track to determine the AHI may be stored at least in part in a memory in the smart phone, laptop, or tablet and executed by a processor also housed in the smart phone, PC, laptop or tablet.

Alternatively or additionally, a computer system for determining the AHI may be located at least in part in a real or virtual computer system that receives the voice track from the recording device. The computer systems may be a centralized system or a distributed system having components and executable instruction sets located in different servers, and may be partially or completely based on access to servers via the internet, that is partially or completely "cloud based". The computer system may have a local or distributed memory comprising a data base of data acquired and/or generated for the population of $\mathcal{N}$ or N persons for use in determining AHI or presence or absence of OSA, in accordance with an embodiment of the invention.

In the description and claims of the present application, each of the verbs, "comprise" "include" and "have", and conjugates thereof, are used to indicate that the object or objects of the verb are not necessarily a complete listing of components, elements or parts of the subject or subjects of the verb.

Descriptions of embodiments of the invention in the present application are provided by way of example and are not intended to limit the scope of the invention. The described embodiments comprise different features, not all of which are required in all embodiments of the invention. Some embodiments utilize only some of the features or possible combinations of the features. Variations of embodiments of the invention that are described, and embodiments of the invention comprising different combinations of features noted in the described embodiments, will occur to persons of the art. The scope of the invention is limited only by the claims.

The invention claimed is:

1. A method of determining a value for an apnea-hypopnea index (AHI) for a person, the method comprising:
   recording, by a sound recorder, a voice track of a person;
   dividing the voice track into frames by a processor;
   extracting a first group of features from the frames of the voice track that characterize the voice track, by a processor;
   associating each frame with a class of phonemes based on said first group of features;
   based on the phonemes associated with each frame, extracting a second group of features from each frame;
   determining, by a processor, feature vectors for the frames based on said second group of features; and,
   processing, by a processor, the feature vectors to determine an AHI.

2. The method according to claim 1 wherein recording the voice track comprises causing the person to vocalize a voice protocol comprising at least one phoneme chosen from at least one or any combination of more than one phoneme group consisting of: phonemes characteristic of vowels and/or phonemes characteristic of nasal sounds.

3. The method according to claim 1 wherein extracting features comprises extracting short term (ST) features, which are features that are statistically stationary during a frame, from each frame and using the ST features to define at least one of the feature vectors for the frame.

4. The method according to claim 3 wherein the short term features comprise at least one feature chosen from at least one or any combination of more than one of: time domain features, spectral domain features, cepstral domain features, and/or hyper-nasal features.

5. The method according to claim 1 further comprising determining a posteriori mean estimate for each phoneme responsive to the feature vectors defined for the phoneme and a universal background Gaussian mixture model (GM-$M_{UBM}$).

6. The method according to claim 5 further comprising using the posteriori mean estimate for each phoneme to determine an AHI for the person.

7. The method according to claim 6 wherein using the posteriori mean estimate for each phoneme comprises concatenating the posteriori mean vectors to generate a super vector for the person.

8. The method according to claim 7 further comprising extracting long term features from the voice track and concatenating at least one long term feature with the posteriori mean vectors to generate the super vector.

9. The method according to claim 7 further comprising using the super vector to determine an AHI for the person.

10. The method according to claim 6 wherein using the posteriori mean estimate for each phoneme comprises determining an estimate for the AHI of the person responsive to the posteriori mean estimate of each phoneme.

11. The method according to claim 1 further comprising concatenating a plurality of the feature vectors to generate a super vector for the person and using the super vector to determine AHI for the person.

12. Apparatus for determining an apnea-hypopnea index (AHI) for a person, the apparatus comprising:
   at least one voice recording device that records a voice track for the person; and
   at least one processor programmed to:
      divide the voice track into frames;
      extract a first group of features from the frames of the voice track that characterize the voice track;
      associate each frame with a class of phonemes based on said first group of features;
      based on the phonemes associated with each frame, extract a second group of features from each frame;
      determine feature vectors for each of the frames based on said second group of features; and
      process the feature vectors to determine an AHI.

13. Apparatus according to claim 12 wherein the at least one processor is additionally programmed to determine a posteriori mean feature vector for each phoneme responsive to the feature vectors defined for frames associated with the phoneme.

14. Apparatus according to claim 13 wherein the at least one processor uses the posteriori mean feature vectors to generate a super vector for the voice track.

15. Apparatus according to claim 14 wherein the at least one processor determines an AHI for the person responsive to the super vector.

* * * * *